(12) United States Patent
Snyder (10) Patent No.: US 6,592,560 B2
(45) Date of Patent: Jul. 15, 2003

(54) URINE RETENTION AND COLLECTION DEVICES FOR INCONTINENT WOMEN

(75) Inventor: Daniel R. Snyder, Branford, CT (US)

(73) Assignee: Matthew G. LaPointe, Novi, MI (US)

( * ) Notice: Subject to any disclaimer, the term of this patent is extended or adjusted under 35 U.S.C. 154(b) by 0 days.

(21) Appl. No.: 09/769,177

(22) Filed: Jan. 25, 2001

(65) Prior Publication Data

US 2001/0037098 A1 Nov. 1, 2001

Related U.S. Application Data

(60) Provisional application No. 60/177,921, filed on Jan. 25, 2000.

(51) Int. Cl.⁷ .................................. A61F 5/44
(52) U.S. Cl. ..................... 604/331; 604/544
(58) Field of Search ................. 604/327–331, 604/544, 355–356; 600/29–32

(56) References Cited

U.S. PATENT DOCUMENTS

| | | | |
|---|---|---|---|
| 3,528,423 A | | 9/1970 | Lee |
| 3,683,914 A | * | 8/1972 | Crowley ..................... 604/329 |
| 4,246,901 A | * | 1/1981 | Michaud ..................... 4/144.3 |
| 4,296,745 A | | 10/1981 | Raymond |
| 4,484,917 A | | 11/1984 | Blackmon |
| 4,795,449 A | * | 1/1989 | Schneider et al. .......... 604/129 |
| 4,822,347 A | | 4/1989 | MacDougall |
| 4,846,819 A | * | 7/1989 | Welch ......................... 600/574 |
| 4,889,533 A | | 12/1989 | Beecher |
| 4,904,248 A | * | 2/1990 | Vaillancourt ................ 604/327 |
| 4,986,823 A | | 1/1991 | Anderson et al. |
| 5,049,144 A | * | 9/1991 | Payton ........................ 600/574 |
| 5,147,301 A | | 9/1992 | Ruvio |
| 5,336,208 A | | 8/1994 | Rosenbluth et al. |
| 5,370,637 A | * | 12/1994 | Brodeur ...................... 4/144.3 |

FOREIGN PATENT DOCUMENTS

| | | |
|---|---|---|
| DE | 22 08 810 A | 8/1973 |
| DE | 24 47 642 A | 1/1976 |
| FR | 1 479 675 A | 5/1967 |
| GB | 2 126 902 A | 4/1984 |
| GB | 2 129 686 A | 5/1984 |
| WO | 97/28767 A | 8/1997 |
| WO | 00/00116 A | 1/2000 |

* cited by examiner

*Primary Examiner*—Weilun Lo
*Assistant Examiner*—C. Lynne Anderson
(74) *Attorney, Agent, or Firm*—Edwards & Angell, LLP; George N. Chaclas, Esq.

(57) ABSTRACT

A feminine care device for collecting urine including a reservoir defining a recess for receiving urine. The reservoir has a rim and flange configured for periurethral sealing and adhesion to the labia minora, respectively. A tab depends from the reservoir for engagement and adhesion to the anterior vaginal wall. A drain for selectively draining urine from the reservoir is provided.

29 Claims, 6 Drawing Sheets

URINE RETENTION AND COLLECTION DEVICES FOR INCONTINENT WOMEN

CROSS-REFERENCE TO RELATED APPLICATION

This application claims priority to U.S. Provisional Patent Application No. 60/177,921, filed Jan. 25, 2000, which is incorporated herein by reference in its entirety.

BACKGROUND OF THE INVENTION

1. Field of the Invention

The subject disclosure relates to devices for aiding female urinary incontinence, and more particularly to an improved female urine collection device which comfortably and discretely conforms to the female body and protects against leakage.

2. Background of the Related Art

Approximately eleven million women in America experience involuntary leakage of urine. Such a condition erodes their quality of life because medical, emotional and social problems often accompany incontinence. Skin rashes, urinary tract infections, sleep disturbances, restricted social interactions, reduced sexual activity, loss of self-esteem and depression are only a few of the typical symptoms associated with incontinence.

For many women, the condition is a consequence of aging and approximately half of the women in nursing homes are incontinent in varying degrees. Further, hospitalized patients, such as those in traction or who are otherwise bedridden must empty their bladder at bedside. Moreover, circumstances may simply make a restroom break inconvenient such as when working in outer space. To accommodate such conditions, it is desirable to provide a device which can comfortably and reliably collect, retain and empty, or channel urine so as to prevent embarrassing and untimely leakage.

Several devices have been developed to perform this function. For example, U.S. Pat. No. 3,528,423 to Lee discloses a female incontinence device having an intravaginal stabilizer bar with projections for holding a face plate in place. The face plate has grooves to conform to the major and minor labia, respectively. The face plate further defines an outlet for allowing urine to collect in a reservoir. A drain tube may terminate in a plug or connect to a suitable receptacle. Buttons on the face plate provide anchors for a harness to secure the device to the patient's body.

A further example includes U.S. Pat. No. 5,370,637 to Brodeur, which discloses a female urination aid to facilitate urination by females in a substantially upright position. A base defines an oval center opening which fits around a patient's vulva. The opening has upper contours and a seal to engage the labia. Finger pads on the base provide an area for the patient to apply pressure to effectuate proper engagement of the seal. An absorbent pad disposed at the bottom of the base can be used as a germicidal and deodorizing wipe. A collapsible fluid guide extends from the base and terminates at an outlet to take urine away from the patient. The fluid guide has an inner liner surrounded by an accordion boot.

Still further, U.S. Pat. No. 4,986,823 to Anderson et al. discloses a device for directing a flow of urine from a female. The device includes a body having a collector surrounding the urethral meatus and a pair of limbs extending internally of the vagina through the vaginal orifice. A collection tube is connected to the collector to communicate the urine into a reservoir. Further, the collector includes torsion members to provide a spring force to separate the limbs. An applicator holds the limbs together for easy insertion.

U.S. Pat. No. 5,336,208 to Rosenbluth et al. discloses a first embodiment having a disposable urinary incontinence pad with a base that has an adhesive layer for providing a fluid tight seal and occlusion against the urethral meatus and increasing retention against the vestibule of the vulva. Lateral edges of the base and an anterior end of the pad are tucked under the labia minora to enhance retention. Moreover, the adhesive layer can be extended onto the labia-engaging surface to further enhance the stability of the device. A handle in the form of a ring or loop of string facilitates removal. A second embodiment has a short protuberance to be received at least partially within the urethral meatus. A third embodiment has a flexible bladder filled with gel. The bladder conforms to the anatomical structure of the external female genitalia, filling the interlabial space, and sealing against the urethral meatus with the aid of an adhesive.

Also, U.S. Pat. No. 4,484,917 to Blackmon discloses a female external catheter formed from a main body having an inlet for receiving urine. An adhesive layer, surrounding the inlet, secures the inlet about the urethral meatus. A stabilizer provides a rigid backing for the adhesive layer. An outlet tube channels urine into a collection bag. U.S. Pat. No. 4,822,347 to MacDougall discloses a female incontinence device with a tubular sheath integral with a funnel and a urine conduit. A pad of adhesive material secures an entry portion around the urethral meatus. The sheath is a highly stretchable latex rubber in order to absorb the energy created by urine surges and, thus, prevent stress upon the adhesive seal. The conduit leads to a leg bag or urine collection vessel.

Notwithstanding the above teachings, there is a need for an improved female urinary incontinence device. Typically, prior art devices are ill-suited for their intended use due to discomfort and potential for leakage, particularly for ambulatory patients. In light of the foregoing, a need exists for a female urinary incontinence device which is comfortable and secure for bedridden and ambulatory patients.

SUMMARY OF THE DISCLOSURE

The subject disclosure is directed to a device to accommodate female urinary incontinence. The device includes a reservoir defining a recess for receiving urine. The reservoir has a rim configured to adhere the device to the periurethral surface and secure its position. A securement tab depends from the device for engagement in the vaginal opening to further secure the position and orientation of the device. Means for selectively draining the reservoir are also provided. Such means preferably includes a selectively actuable check valve. In another embodiment, an adhesive flange depends from the rim for engaging the labia minora. In use, an adhesive coating is applied to the tab and a string is attached to the tab. The tab has a plurality of hinges to allow the tab to conform to the vaginal opening.

The method for collecting female urine includes the step of providing a collection device having a securing portion with a rim defining an inlet and configured to surround a urethra and engage a labia. A tab is adjacent to the rim and configured for insertion into a vaginal opening to secure a position of the securing portion. The method further includes the steps of applying an adhesive to the rim, adhering the rim to the periurethral surface to create a seal therewith and inserting the tab into the vaginal opening.

These and other unique features of the system disclosed herein will become more readily apparent from the following description and the accompanying drawings.

BRIEF DESCRIPTION OF THE DRAWINGS

So that those having ordinary skill in the art to which the disclosed device appertains will more readily understand how to make and use the same, reference may be had to the drawings wherein.

DETAILED DESCRIPTION OF THE PREFERRED EMBODIMENT

The subject disclosure relates to an improved system for capturing the urine of women. The system is particularly applicable to women who are incontinent or bed-ridden, although the system may be utilized in many circumstances in which insertion of a catheter into the urethra is contraindicated for medical reasons or such as during a long journey when a bathroom is unavailable, as would be readily appreciated by those skilled in the art.

The present disclosure overcomes many problems of the prior art associated with female urinary aids. The advantages, and other features of the system disclosed herein, will become more readily apparent to those having ordinary skill in the art from the following detailed description of certain preferred embodiments of the invention taken in conjunction with the figures which set forth representative embodiments of the present disclosure.

Figure 1:
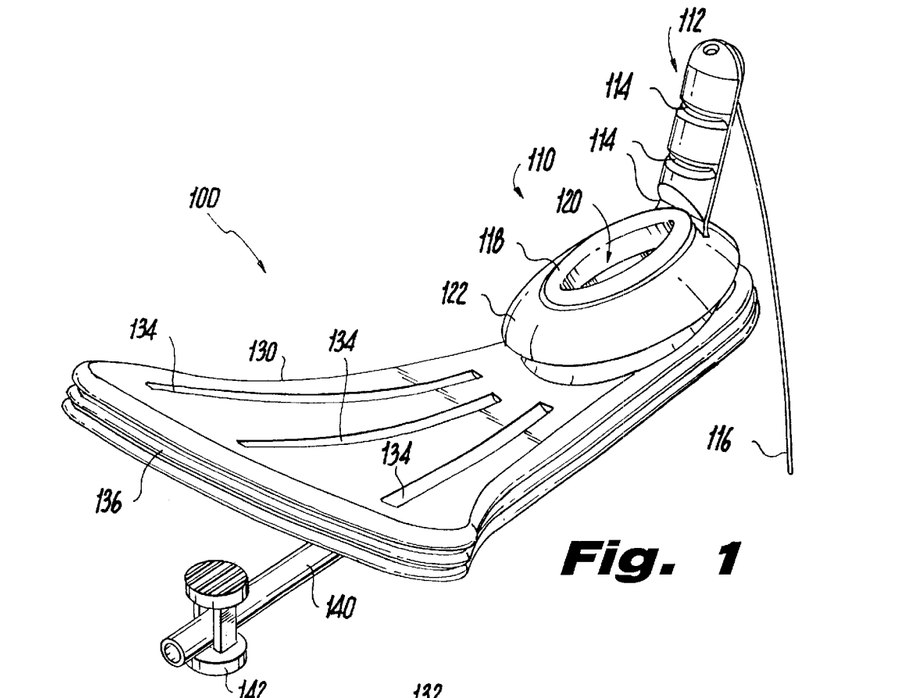
FIG. 1 is a front perspective view of a first urinary incontinence device constructed in accordance with a preferred embodiment of the subject disclosure.

Referring to FIG. 1, there is shown urinary incontinence device constructed in accordance with a preferred embodiment of the subject disclosure and designated generally by reference numeral 100. In general, the device 100 includes a securing portion 110 to sealingly engage a patient, a carriage 130 for storing urine and a drain tube 140. In operation, the patient is ambulatory yet micturation is captured for subsequent release. The device 100 is secured in place as easily as a tampon and remains hidden under the patient's clothing in a manner superior to diapers and pads. The drain tube 140 allows the patient to selectively empty the reservoir body.

With continuing reference to FIG. 1, the securing portion 110 includes an elongated tab 112 which serves to secure the device 100 in place. The tab 112 is sized and shaped for insertion into the vaginal opening 180 of the patient. Preferably, the tab 112 is constructed of nylon, styrene, flexible polyvinyl plastic or the like. Hinges 114 integral with the tab 112 create flexibility which helps the tab 112 conform to the patient's anatomy. In one embodiment, the upstanding tab 112 is coated with a bio-compatible adhesive to secure placement of the tab 112 and therefore the device 100 in place. The bio-compatible adhesive preferably does not alter the bacteria flora balance of the vaginal track. A string 116 in combination with the hinges 114 facilitates easy removal of the tab 112 from the vaginal opening 180. In one embodiment, the adhesive on the tab 112 is pressure sensitive and contains a hydrophilic resin. Further, the coating weight of the adhesive on the tab 112 should be set to maximize wet adhesion and wet shear resistance. In another embodiment, a water soluble adhesive based upon polyvinylmethyl ether may be used. In yet another embodiment, the tab 112 has a plurality of protuberances (not shown) to engage the vaginal rugae and help secure the tab 112 in place.

Figure 4:
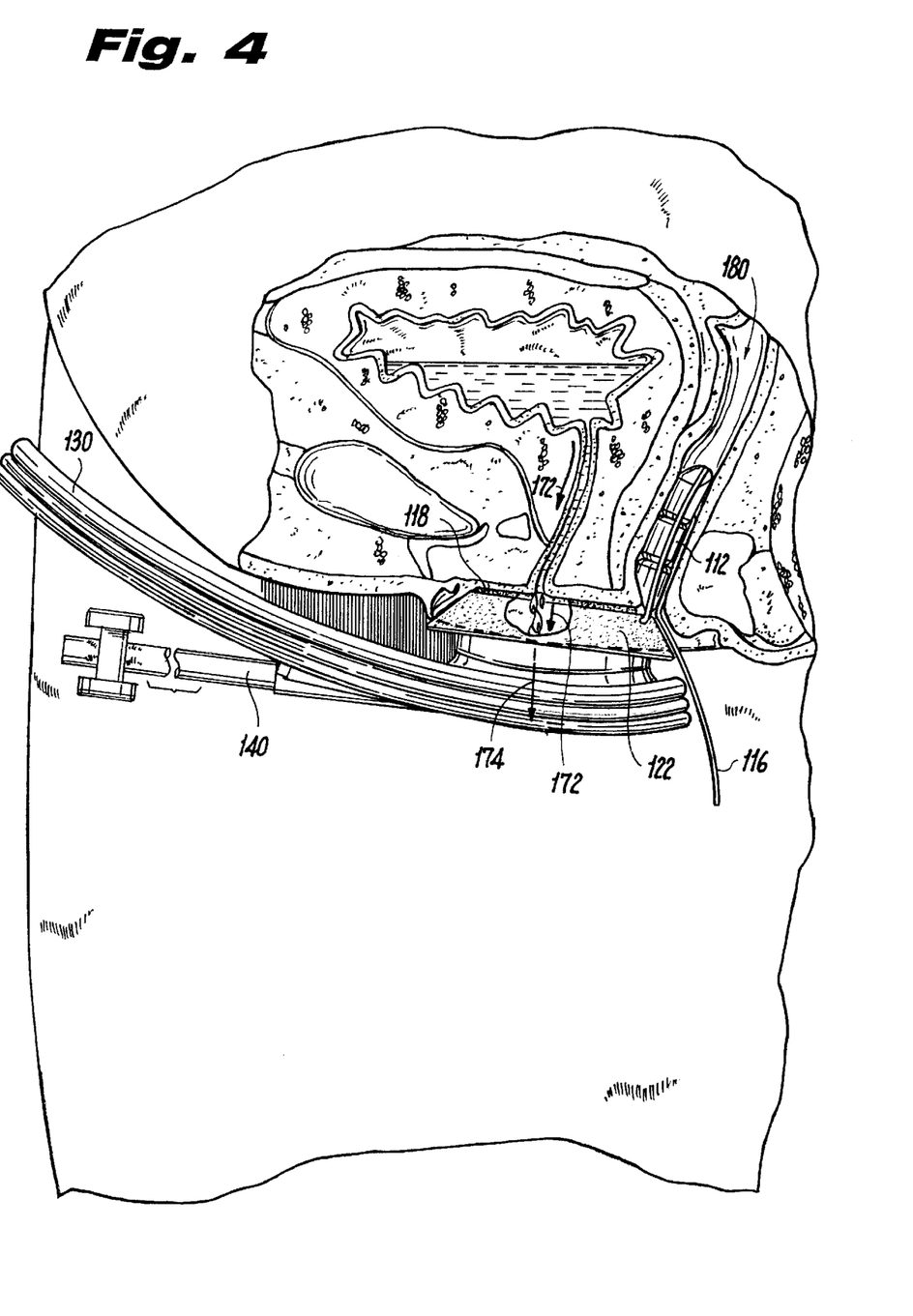
FIG. 4 is a side-elevational view of the urinary incontinence device of FIG. 1 fully disposed in an operational position on a patient.

The securing portion 110 also includes a rim 118 sized and configured to sealingly engage the labia minora of the patient (see FIG. 4). The rim 118 defines an inlet 120 which surrounds the urethra of the patient. Preferably, the tab 112 is disposed adjacent the rim 118 and projects at approximately a 45–50 degree angle so that it corresponds with that of the typical vaginal axis. Preferably, the rim 118 is composed of a malleable material, such as rubber, so that it readily conforms to the anatomy of the patient. It is envisioned that in order to effectively seal around the urethra, the rim 118 is coated with a bio-compatible adhesive appropriate to the corresponding contact area with the patient. In one embodiment, the adhesive of the rim 118 swells and becomes sticky upon contact with moisture. Further, the rim 118 may have a groove (not shown) which is filled with adhesive. In a preferred embodiment, the groove has a depth of 0.0015 to 0.0020 inches.

The securing portion 110 also includes a flange 122 surrounding the rim 118. The flange 122 engages the labia minora to help secure the rim 118 in place on the patient. Preferably, the flange 122 is constructed of nylon, styrene, flexible polyvinyl plastic or the like. In one embodiment, a sticky adhesive is hot melt onto the flange 122 to create the securement of the flange 122 to the labia minora. In another embodiment, the flange 122 is provided with double-sided tape. In still another embodiment, the flange 122 is provided with adhesive by a vacuum transfer process. The adhesive should be bio-compatible with respect to the contact area. Further, the adhesive may contain a moisture absorbent component such as carboxy methyl cellulose to enhance adhesion. In yet embodiment, no flange is required.

Still referring to FIG. 1, the carriage 130 depends from the rim 118 of the securing portion 110 to collect urine as it evacuates the patient. Preferably, the carriage 130 is sized and configured for free movement of the patient and concealment under traditional clothing. When empty as shown, the carriage 130 compresses to maximize comfort and minimize obtrusiveness. It is envisioned that the top surface 132 of the carriage 130 is a flexible polyvinyl plastic in order to provide shape and support. In one embodiment, a plurality of channels 134 in the top surface 132 of the carriage 130 provide additional structural support. A plurality of bellows portion 136 depends from the top surface 132 of carriage 130 to allow for expansion as urine collects therein. The bellows portion 136 is preferably elastomeric in construction.

A drain tube 140 depends from carriage 130 for allowing the patient to release urine collected therein. The drain tube 140 has a manual release valve 142 to allow selective opening of the drain tube 140 by the patient. Alternatively, the drain tube 140 terminates with a check valve that opens and closes with the use of a pull tab (not shown). In yet another embodiment, the drain tube 140 terminates in a collection bag (not shown). In still another embodiment, the drain tube 140 includes an internal pinch valve.

It is also envisioned that the drain tube 140 allows cleansing and medicating of the vaginal area without removal of the device 100. For cleansing, the patient would introduce a cleaning solution such as water into the carriage 130 by way of the drain tube 140. For medicating, the patient would introduce by way of the drain tube 140 a therapeutic solution. The therapeutic solution would be varied according to the condition of the patient such as an anti-inflammatory agent, an antibiotic, a fungicide or the like.

Figure 2:
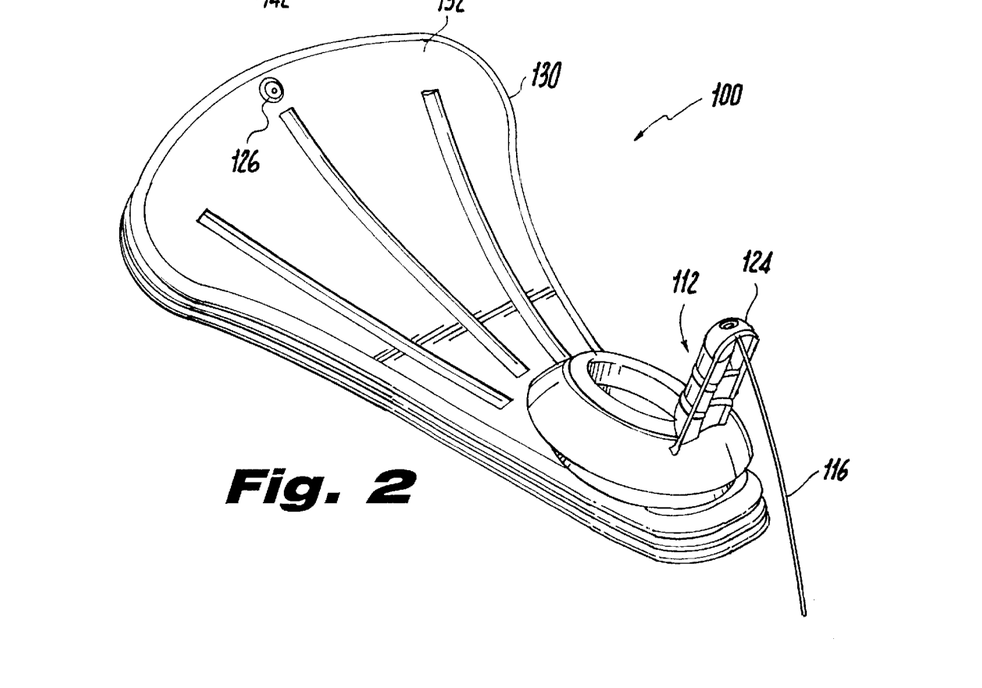
FIG. 2 is a rear perspective view of the urinary incontinence device of FIG. 1.

Referring to FIG. 2, the string 116 is preferably attached to a distal end 124 of the upstanding tab 112 to facilitate easy removal of the device 100 by minimizing the effort required to remove the tab 112. In one embodiment, the top surface 132 of the carriage 130 contains a leak proof air vent 126. The air vent 126 allows efficient emptying of the carriage 130 without creating a vacuum effect therein.

It should be recognized that although "patient" is used throughout the specification to refer to a woman utilizing the subject system, the patient may be ambulatory and other than minor urinary incontinence perfectly healthy. For simplicity, the subject application describes a patient inserting and removing the subject invention, however, it is also envisioned that a caregiver may insert, empty and remove the device 100. Preferably, the patient uses their hands to insert the device 100.

Figure 3:
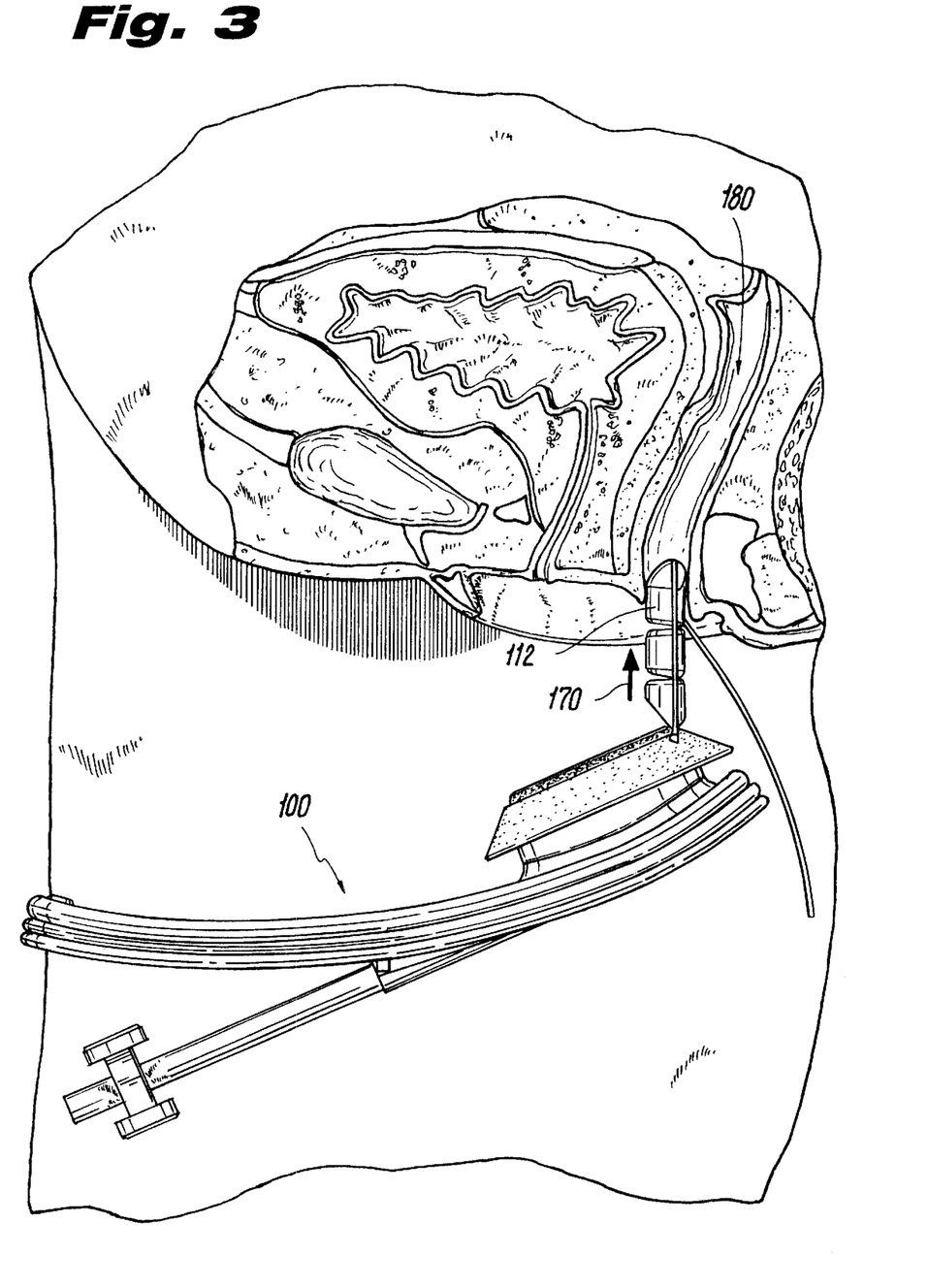
FIG. 3 is a side-elevational view of the urinary incontinence device of FIG. 1 during insertion of the securement tab into the vaginal opening of a patient.

Referring to FIG. 3, to apply the device 100, a patient inserts the tab 112 into the vaginal opening along the direction indicated by arrow 170. If the adhesives are coated with silicone coated release paper (not shown), the patient removes the silicone coated release paper or similar non-sticking packaging in preparation for use of the device 100.

Referring to FIG. 4, during application the patient fully engages the tab 112 within the vaginal opening to locate the rim 118 around the urethra. The device 100 is secured in place sufficiently to withstand greater than 100 mmHg output pressure of the urethral sphincter and contain up to 400 ml of micturation. As a result, when the bladder evacuates through the urethra, the urine passes through the inlet 120 in the direction indicated by arrows 172 into the carriage 130.

It is envisioned that the tab 112 can be held in place due to the pressure from the wall of the vaginal opening. When the tab 112 is coated with a pressure sensitive adhesive, the pressure from the wall of the vaginal opening will create additional adhesive tension. Similarly, if the tab 112 has protuberances (not shown) provided thereon, the pressure from the wall of the vaginal opening will create additional structural tension with the protuberances.

Still referring to FIG. 4, when pressure is applied on the rim 118, it conforms to the surface of the labia minora. Preferably, an adhesive on the rim 118 swells and becomes sticky to create a periurethral leak-proof seal. As the flange 122 engages the labia minora, the rim 118 is further affixed about the urethra. Preferably, the flange 122 is pressed into place to engage an adhesive thereon in contact with the labia minora.

The forward portion of the carriage 130 and the drain tube 140 can be flexed to rest against the patient's lower abdomen. Thus, the obtrusiveness of the device 100 is minimized. As the carriage 130 collects urine, the plurality of bellows portion 136 expands outwardly in the direction indicated by arrow 174. When the carriage 130 is full of urine, the urine may splash undesirably while a patient moves. Further, the splashing may cause partial leakage about the rim 118. Under such circumstances, it is envisioned that a reticulated polyurethane foam (not shown) in the carriage 130 will absorb the urine to prevent sloshing and the associated undesirable effects and will add only minimal weight.

Figure 5:
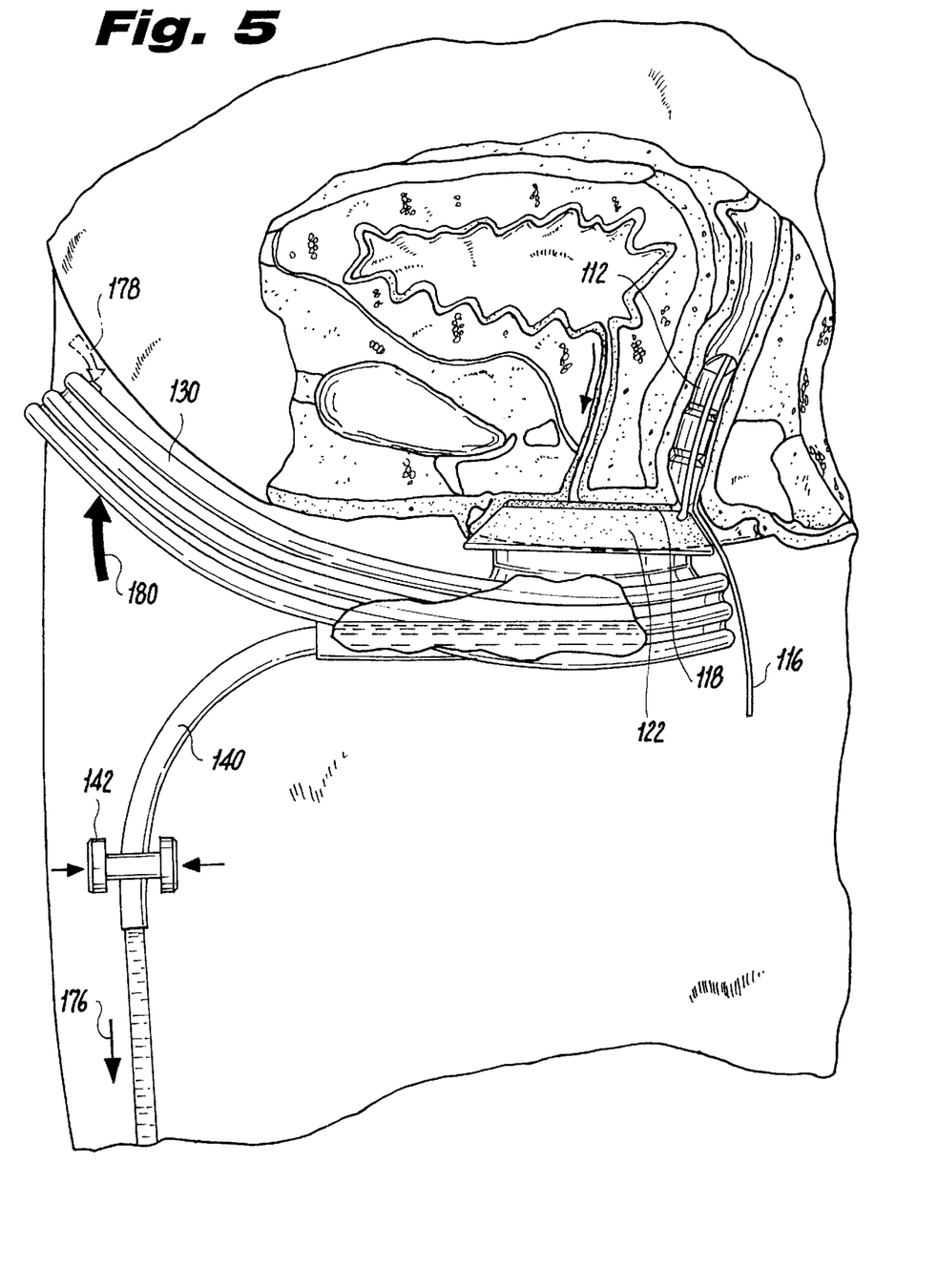
FIG. 5 is a side-elevational view of the urinary incontinence device as in FIG. 4 with the reservoir shown in partial cross-section as urine is drained therefrom.

Referring to FIG. 5, to empty the carriage 130, the patient positions the drain tube 140 over a toilet and opens or removes the valve 142 to allow the urine to exit out of the drain tube 140 in the direction indicated by arrow 176. The patient may be lying down, sitting or standing to evacuate the carriage 130. As urine exits, air enters air vent 126 in the direction indicated by arrow 178 and the plurality of bellows portion 136 compresses in the direction indicated by arrow 180. When evacuation of the carriage 130 is complete, the drain tube 140 is again blocked by the valve 142 and the patient can once again return to normal activity. It is envisioned that the patient may apply the device 100 and wear it for extended periods while evacuating the carriage 130 multiple times as may be required. When removal of the device 100 is desired, the patient can grasp the string 116 and remove the tab 112 from the vaginal opening. If the rim 118 and flange 122 are provided with adhesives, they can be manually peeled away from the periurethral surface and the labia minora, respectively.

Figures 6, 7:
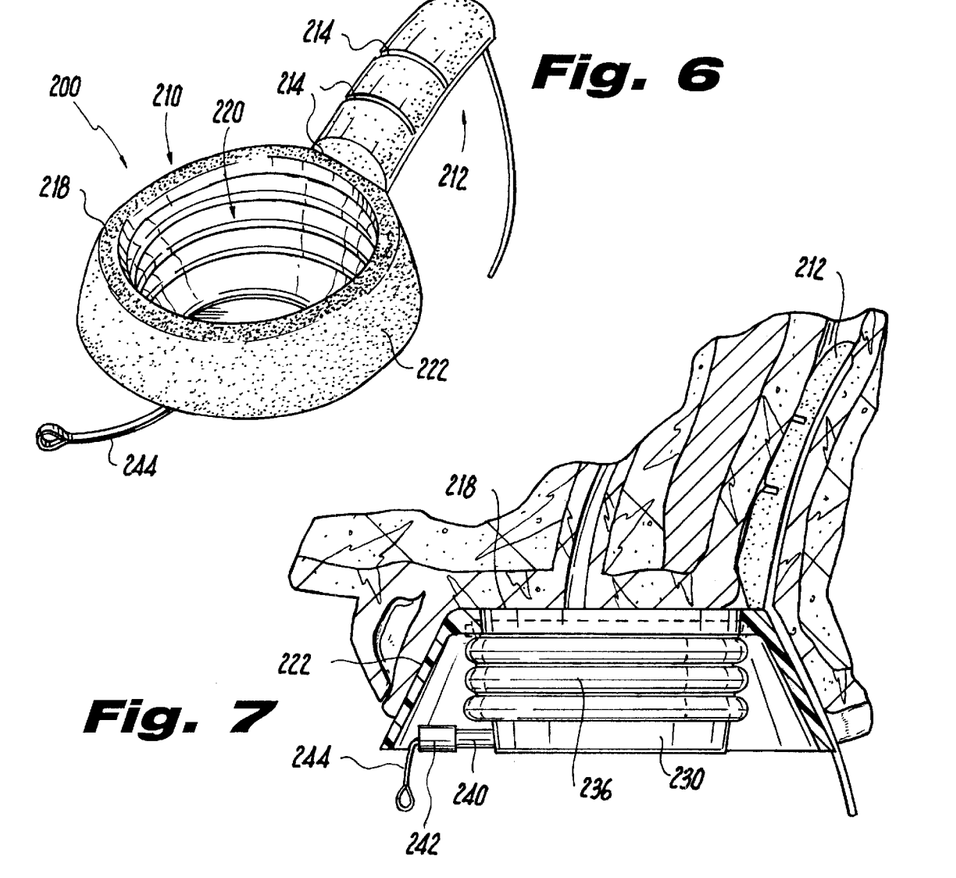
FIG. 6 is a perspective view of a second urinary incontinence device constructed in accordance with a preferred embodiment of the subject disclosure.
FIG. 7 is a side-elevational view of the urinary incontinence device of FIG. 6 in an operational position on a patient.

Referring to FIG. 6, another device constructed in accordance with the subject disclosure is illustrated and designated generally by reference numeral 200. In general, device 200 includes a securing portion 210 to sealingly engage a patient, a reservoir body 210 for storing urine and a drain (not shown). In operation, the patient is ambulatory, the device 200 remains hidden and the patient can selectively empty the reservoir body.

The securing portion 210 includes an elongated tab 212 which serves to secure the device 200 in place. Preferably, the hinges 214 create flexibility which helps the tab 212 conform to the patient's anatomy. The upstanding tab 212 is coated with a bio-compatible adhesive to further secure placement of the tab 212 and therefore the device 200 in place.

The securing portion 210 also includes a rim 218 sized and configured to sealingly engage the periurethral surface of the patient. The rim 218 defines an inlet 220 which surrounds the urethra of the patient. It is envisioned that in order to effectively seal around the urethra, the rim 218 is malleable and coated with an adhesive. In one embodiment, the adhesive of the rim 218 swells and becomes sticky upon contact with moisture.

The securing portion 210 also includes a flange 222 surrounding the rim 218. The flange 222 engages the labia minora to help secure the rim 218 in place periurethrally on the patient. Preferably, a sticky adhesive is hot melt or vacuum transferred onto the flange 222 to create the securement of the flange 222 to the labia minora. In another embodiment, the flange 222 is provided with double-sided tape.

Referring now to FIG. 7, the reservoir body includes a diaphragm 230 depending from the rim 218 to collect urine as it evacuates the patient. Preferably, the diaphragm 230 is sized and configured to be contained within the flange 222 when empty. Further, the diaphragm 230 is preferably elastomeric in construction to provide additional expansion and absorption of the energy of evacuating urine. The diaphragm 230 defines a drain 240 for allowing the patent to release urine collected therein. The drain 240 is an opening at the lowest part of the diaphragm 230. Release 244 allows the patient to manually open the drain 240.

In use, the patient fully engages the tab 212 within the vaginal opening to locate the rim 218 around the urethra. It is envisioned that the tab 212 is held in place due to the pressure from the wall of the vaginal opening and adhesive tension. As a result, when the bladder evacuates through the urethra, the urine passes into the diaphragm 230. The diaphragm 230 defines a plurality of bellows 236 to allow for expansion as urine collects therein.

When pressure is applied on the rim 218, the rim 218 conforms to the periurethral surface. Preferably, an adhesive on the rim 218 swells and becomes sticky to create a periurethral leak-proof seal. As the flange 222 engages the labia minora, the rim 218 is further affixed about the urethra. Preferably, the flange 222 is pressed into place to engage an adhesive thereon. The drain 240 extends away from the patient at the lowest point of the diaphragm 230. The drain 240 is normally blocked with a one-way valve (not shown) or an end plug 242 which is attached to a release 244.

Figure 8:
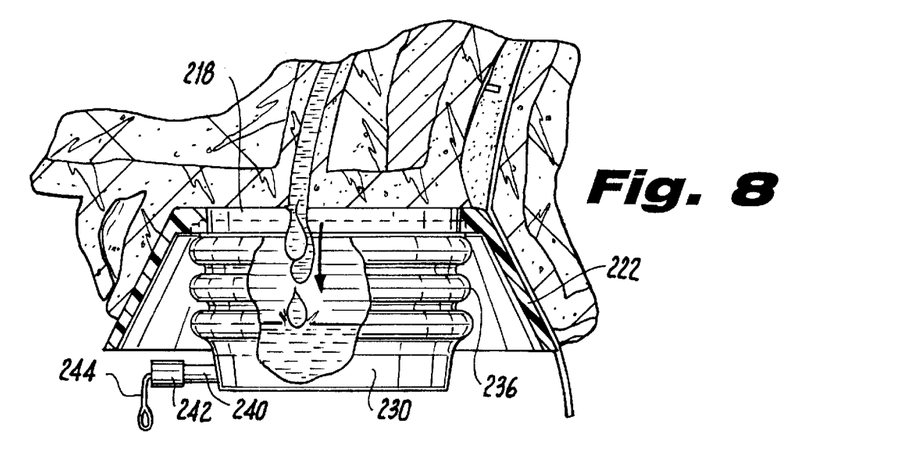
FIG. 8 is a partial cross-sectional view of the urinary incontinence device of FIG. 6 in an operational position on a patient as urine is received in the reservoir.

Referring now to FIG. 8, when the device 200 is in place on a patient, the rim 218 surrounds the urethra exit point. As a result, when the bladder evacuates through the urethra, the urine passes into the diaphragm 230. As the diaphragm 230 collects urine, the plurality of bellows 236 expand downward. Preferably, the diaphragm 230 is constructed of elastomeric material to allow further expansion. When the diaphragm 230 is full of urine, the patient may empty the diaphragm 230 from the drain 240. Preferably, the drain 240 extends from the low point of the diaphragm 230 to facilitate complete evacuation of the diaphragm 230. It is envisioned that the patient will empty the device 200 into the toilet. Alternatively, the patient may empty the device 200 into a receptacle for subsequent disposal. To open the drain 240, the end plug 242 is removed by pulling the release 244.

Figure 9:
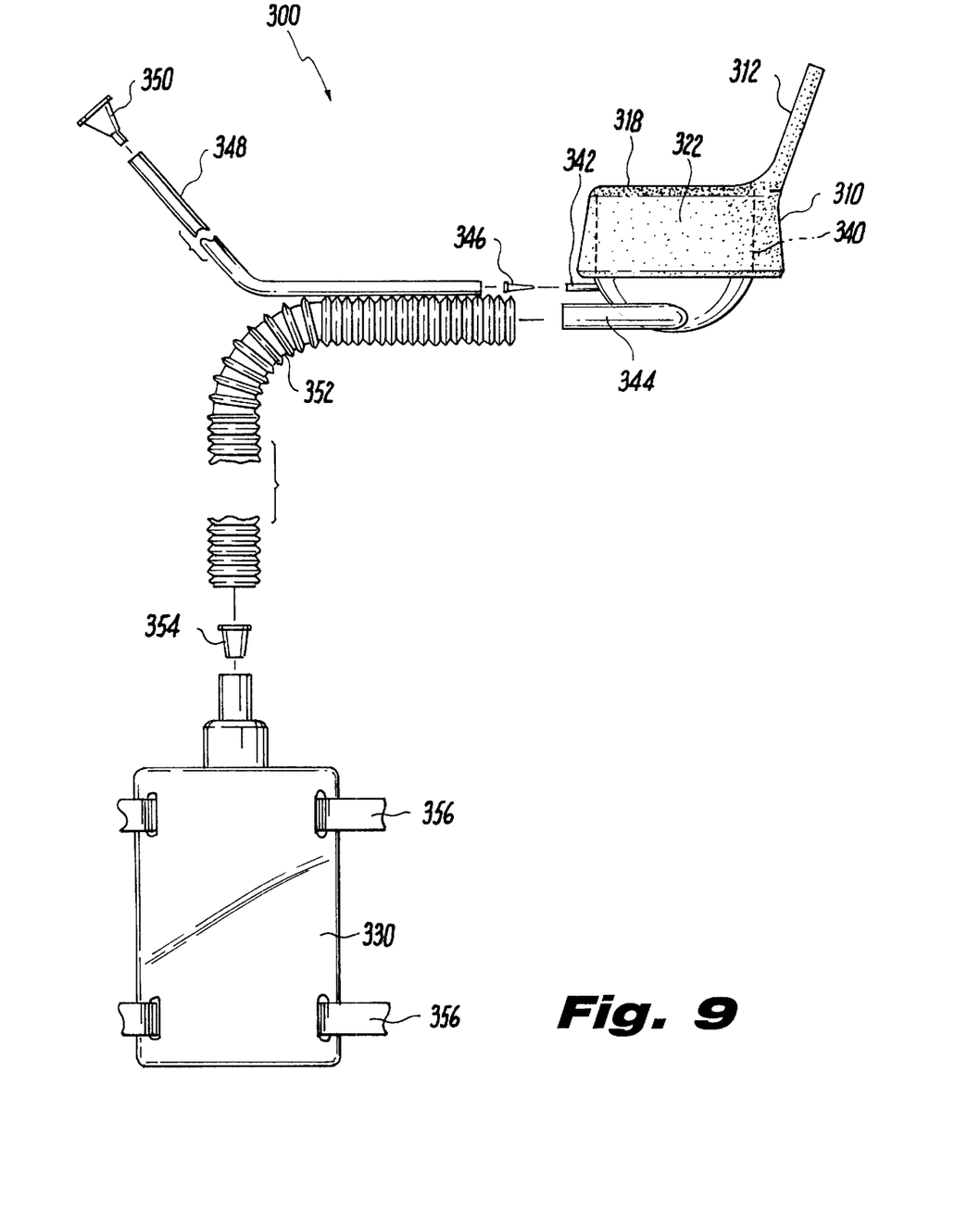
FIG. 9 is an illustration of a urine collection system constructed in accordance with a preferred embodiment of the subject disclosure.

Referring now to FIG. 9, there is disclosed a urine collection system constructed in accordance with the subject disclosure and designated generally by reference numeral 300. The system 300 includes a securing portion 310 to sealingly engage a patient, a collection portion for storing urine and an irrigation portion for cleansing the vaginal area. In operation, the securing portion 310 engages the patient to capture micturation in a bag 330 of the irrigation portion for subsequent release. The irrigation portion allows the patient to cleanse and medicate the vaginal area of the patient.

The securing portion 310 includes a tab 312 which serves to secure the system 300 in place. The tab 312 is sized and shaped for insertion into the vaginal opening of the patient. Preferably, the tab 312 is coated with an adhesive to secure the tab 312 within the vaginal opening. The tab 312 does not have a string and is removed by grasping. In another embodiment, a string is fixed on a distal end of the tab 312 to facilitate removal from the vaginal opening.

The securing portion 310 also includes a rim 318 sized and configured to sealingly engage the periurethral surface of the patient. The rim 318 defines an inlet which surrounds the urethra of the patient. Preferably, the rim 318 is coated with a bio-compatible adhesive appropriate to the corresponding contact area with the patient. The securing portion 310 also includes a flange 322 surrounding the rim 318. The flange 322 engages the labia minora to help secure the rim 318 in place on the patient. Preferably, the flange 322 is coated with a bio-compatible adhesive to enhance engagement with the patient.

With continuing reference to FIG. 9, the collection portion includes a syphon portion 340, shown partially in phantom lines, depending from the rim 318 of the securing portion 310 to collect urine as it evacuates the patient. The syphon portion 340 terminates in a tube for irrigation 342 and a tube for urine collection 344. In another embodiment, the syphon portion 340 is funnel-shaped. Preferably, the irrigation tube 342 terminates with a one-way check valve 346 to prevent fluid from entering the irrigation tube 342. A conduit 348 connects to the irrigation tube 342 for delivering topical medical and irrigation solutions. The conduit 348 has a female Luer end 350 to facilitate the introduction of solutions into the conduit 348 through the one-way check valve 346 and into the syphon portion 340 for receiving a cleansing or medicating solution. It is envisioned that the irrigation portion may be adapted for use with each of the urinary incontinence devices disclosed herein. Once in the syphon portion 340, fluids will wash over the vaginal area within the inlet of the rim 318.

The urine collection tube 344 allows the urine and fluid collected in syphon portion 340 to pass into a flexible tube 352. In another embodiment, the urine collection tube 344 has a leak-proof air vent which allows air into the system 300 but prevents urine from leaking. The flexible tube 352 is reticulated and allows routing in a convenient manner. The flexible tube 352 empties into the bag 330. The bag 330 has a check valve 354 at its entry to prevent backflow. Alternatively, the urine collection tube 344 may include a pinch valve or squeeze valve to allow bi-directional flow unless manually closed. Such a configuration allows solutions introduced via irrigation portion to be maintained with the syphon portion 340 to more thoroughly wash the vaginal area.

The bag 330 has straps 356 to fasten to the lower leg of the patient. When full, the patient removes the straps 356, detaches the bag 330 from the reticulated tube 352, empties the bag 330 and reattaches the bag 330 to the reticulated tube 352 and restraps the bag 330 on their lower leg. In another embodiment for bedridden patients, the bag 330 mounts on a bed frame or adjacent structure. It is envisioned that when the irrigation tube 342 is used, the cleansing and medicinal solutions are collected in the bag 330 for disposal.

While the disclosure has been described with respect to preferred embodiments, those skilled in the art will readily appreciate that various changes and/or modifications can be made thereto without departing from the spirit or scope as defined by the appended claims.

What is claimed is:

1. A feminine care device for selectively storing urine comprising:
   a reservoir or storing urine and defining a recess for collecting urine, said reservoir having a rim configured for adhesion to a periurethral surface, an elongated tab adjacent to the rim and upstanding from said reservoir at an angle corresponding to a vaginal axis such that only the elongated tab is inserted within a vaginal opening to secure the device in a stable position and a drain for selectively draining urine from said reservoir.

2. A device as recited in claim 1, further comprising an adhesive flange depending from the rim for engaging the labia minora.

3. A device as recited in claim 1, further comprising an adhesive coating on the tab for adhering to the anterior vaginal surface.

4. A device as recited in claim 1, further comprising a string attached to the tab.

5. A device as recited in claim 1, wherein the tab has a plurality of hinges to allow the tab to conform to the vaginal opening.

6. A feminine care device for urine collection and storage, comprising:
   a) a securing portion having a rim defining an inlet and configured to surround a urethra and engage a periurethral surface, wherein an adhesive applied to the rim creates a seal with the periurethral surface;
   b) a tab adjacent to the rim which is sized and configured for insertion into a vaginal opening to engage a portion of a vaginal wall adjacent to the vaginal opening to secure a position of the securing portion as a weight of the feminine care device increases from storing urine;
   c) an expandable collection portion depending from the rim and supported by the tab, the expandable collection portion for receiving and retaining urine passing through the inlet; and
   d) a drain in fluid communication with the collection portion for selectively discharging urine from the collection portion.

7. A device as recited in claim 6, wherein the adhesive swells and becomes adherent upon contact with moisture.

8. A device as recited in claim 6, further comprising an adhesive flange depending from the rim for engaging the labia and release paper covering the adhesive flange.

9. A device as recited in claim 6, further comprising an adhesive coating on the tab.

10. A device as recited in claim 6, further comprising a release string attached to a distal end of the tab for removing the device.

11. A device as recited in claim 6, wherein the tab has a plurality of hinges to enable the tab to conform to the vaginal opening.

12. A device as recited in claim 6, wherein the collection portion has a flexible top surface and a plurality of expandable bellows depending from the top surface.

13. A device as recited in claim 12, further comprising an air vent in the top surface.

14. A device as recited in claim 6, wherein the drain includes a flow control device operatively associated therewith.

15. A device as recited in Claim 6, wherein the collection portion has at least one expandable bellows depending from the rim for expansion to accommodate urine retained in the collection portion.

16. A device as recited in claim 6, wherein the collection portion has an elastomeric pouch depending from the rim.

17. A device as recited in claim 6, wherein the collection portion is funnel shaped and narrows to the drain.

18. A device as recited in claim 17, further comprising:
   a) a flexible tube connected to the drain;
   b) a reservoir bag connected to the flexible tube; and
   c) a check valve intermediate the flexible tube and the reservoir bag, wherein the drain has an air vent.

19. A device as recited in claim 6, further comprising:
   a) an irrigation tube extending from the collection portion; and
   b) a check valve associated with the irrigation tube for allowing introduction of a fluid to an area surrounded by the rim.

20. A feminine care device for retaining urine comprising:
   a rim defining a recess for receiving urine, said rim configured for adhesion to a periurethral surface of a patient;
   a carriage depending from the rim for retaining the urine, the carriage being sized and configured for concealment and free movement of the patient;
   a tab upstanding from said rim for engagement within a vaginal opening of the patient, wherein only the tab is inserted in the vaginal opening; and
   a drain depending from the carriage for selectively draining the urine therefrom.

21. A feminine care device for retaining urine as recited in claim 20, wherein the carriage is elongated having a narrow end adjacent the rim for comfortably fitting between legs of the patient and a broad end for comfortably resting against a lower abdomen of the patient.

22. A feminine care device for retaining urine as recited in claim 20, wherein the carriage has a top surface for providing shape and support and a plurality of bellows depending from the top surface for allowing expansion as the urine collects therein.

23. A feminine care device for retaining urine as recited in claim 20, further comprising reticulated polyurethane foam within the carriage for preventing sloshing of the urine.

24. A feminine care device for temporarily collecting urine comprising:

a reservoir having a rim defining a recess for receiving urine and configured to sealingly enrage a labia minora of a patient, a storage portion depending from the rim for collecting the urine, and a flange adjacent to and surrounding the rim for securing the rim in place;

a first adhesive on the rim;

a second adhesive on the flange, wherein the first and second adhesives are different;

a tab adjacent to the rim and upstanding from the reservoir at an angle approximately that of a vaginal axis of the patient for engagement within a vaginal opening; and a drain for selectively draining urine from the reservoir.

25. A feminine pare device for collecting urine from a female comprising:

a reservoir defining a recess for receiving urine, said reservoir having a malleable rim configured for engagement to a periurethral surface, an elongated tab adjacent to the rim and upstanding from said reservoir for insertion within a vaginal opening of the female to secure the device in a stable position and a drain for selectively draining urine from said reservoir, wherein the elongated tab has a plurality of hinges to allow the tab to conform to the vaginal opening.

26. A feminine pare device as recited in claim 25, further comprising a string attached to the elongated tab.

27. A feminine care device for retaining urine comprising:

a rim defining a recess for receiving urine, said rim being malleable to readily conform to an anatomy of a patient;

a carriage depending from the rim for retaining the urine, the carriage being sized and configured for concealment and free movement of the patient;

reticulated polyurethane foam within the carriage for preventing sloshing of the urine;

a tab upstanding from said rim for engagement within a vaginal opening of the patient; and a drain depending from the carriage for selectively draining the urine therefrom.

28. A feminine care device for retaining urine as recited in claim 27, wherein the carriage is elongated having a narrow end adjacent the rim for comfortably fitting between legs of the patient and a broad end for comfortably resting against a lower abdomen of the patient, and the carriage has a top surface for providing shape and support, and the carriage has a plurality of bellows depending from the top surface for allowing expansion as the urine collects therein.

29. A feminine care device for retaining urine as recited in claim 27, further comprising reticulated polyurethane foam within the carriage for preventing sloshing of the urine.

* * * * *